US011598758B2

(12) United States Patent
Sirota et al.

(10) Patent No.: US 11,598,758 B2
(45) Date of Patent: Mar. 7, 2023

(54) DETERMINATION OF ASPHALTENE SOLUBILITY DISTRIBUTION

(71) Applicant: ExxonMobil Technology and Engineering Company, Annandale, NJ (US)

(72) Inventors: Eric B. Sirota, Flemington, NJ (US); Bridget E. Lang, Morristown, NJ (US); Birbal Chawla, Sterling, VA (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 435 days.

(21) Appl. No.: 16/930,691

(22) Filed: Jul. 16, 2020

(65) Prior Publication Data

US 2021/0018477 A1    Jan. 21, 2021

Related U.S. Application Data

(60) Provisional application No. 62/875,552, filed on Jul. 18, 2019.

(51) Int. Cl.
    *G01N 1/22*           (2006.01)
    *G01N 31/02*         (2006.01)
              (Continued)

(52) U.S. Cl.
    CPC ............ *G01N 31/02* (2013.01); *G01N 13/00* (2013.01); *G01N 21/47* (2013.01); *G01N 33/2835* (2013.01); *G01N 2030/8854* (2013.01)

(58) Field of Classification Search
    CPC .... G01N 30/02; G01N 33/28; G01N 33/2835; G01N 31/02; G01N 21/47; G01N 13/00; Y10T 436/21
    USPC .......... 356/246, 432–440, 70, 335–343, 300, 356/311, 517; 436/178–181; 210/656; 250/458.1
    See application file for complete search history.

(56) References Cited

U.S. PATENT DOCUMENTS

| | | | |
|---|---|---|---|
| 5,871,634 A | 2/1999 | Wiehe et al. | |
| 7,875,464 B2 * | 1/2011 | Schabron | ............... G01N 30/02 436/55 |

(Continued)

*Primary Examiner* — Hoa Q Pham
(74) *Attorney, Agent, or Firm* — Vorys, Sater, Seymour and Pease LLP

(57) ABSTRACT

Systems and methods are provided for determining an asphaltene solubility distribution for a petroleum sample and/or other hydrocarbon sample. A vessel for performing the method can include both packing material(s) and sidewall(s) that correspond to substantially inert materials. The vessel can initially contain a precipitating solvent suitable for causing precipitation of asphaltenes from a hydrocarbon sample. Examples of a precipitating solvents can correspond to n-heptane, toluene, and mixtures of n-heptane and toluene. The petroleum sample is then introduced into the vessel, along with a carrier solvent. The volume of the precipitating solvent can be large relative to the sample, so that the solubility of asphaltenes in the sample becomes dependent on the properties of the precipitating solvent. If asphaltenes are precipitated, the asphaltenes can be washed out of the column using a dissolution solvent. The asphaltenes washed out using the dissolution solvent can then be characterized to determine a total asphaltene content.

20 Claims, 1 Drawing Sheet

(51) Int. Cl.
*G01N 33/28* (2006.01)
*G01N 21/47* (2006.01)
*G01N 13/00* (2006.01)
G01N 30/88 (2006.01)

(56) References Cited

U.S. PATENT DOCUMENTS

| | | |
|---|---|---|
| 8,241,920 B2 | 8/2012 | Schabron et al. |
| 8,269,961 B2 * | 9/2012 | Mostowfi ............ G01N 33/2823 356/326 |
| 8,367,425 B1 * | 2/2013 | Schabron ............... G01N 33/28 436/181 |
| 9,068,962 B2 * | 6/2015 | Schneider ............... B01F 33/30 |
| 2005/0013740 A1 | 1/2005 | Mason et al. |
| 2011/0120950 A1 * | 5/2011 | Schabron ............... G01N 30/02 250/281 |

* cited by examiner

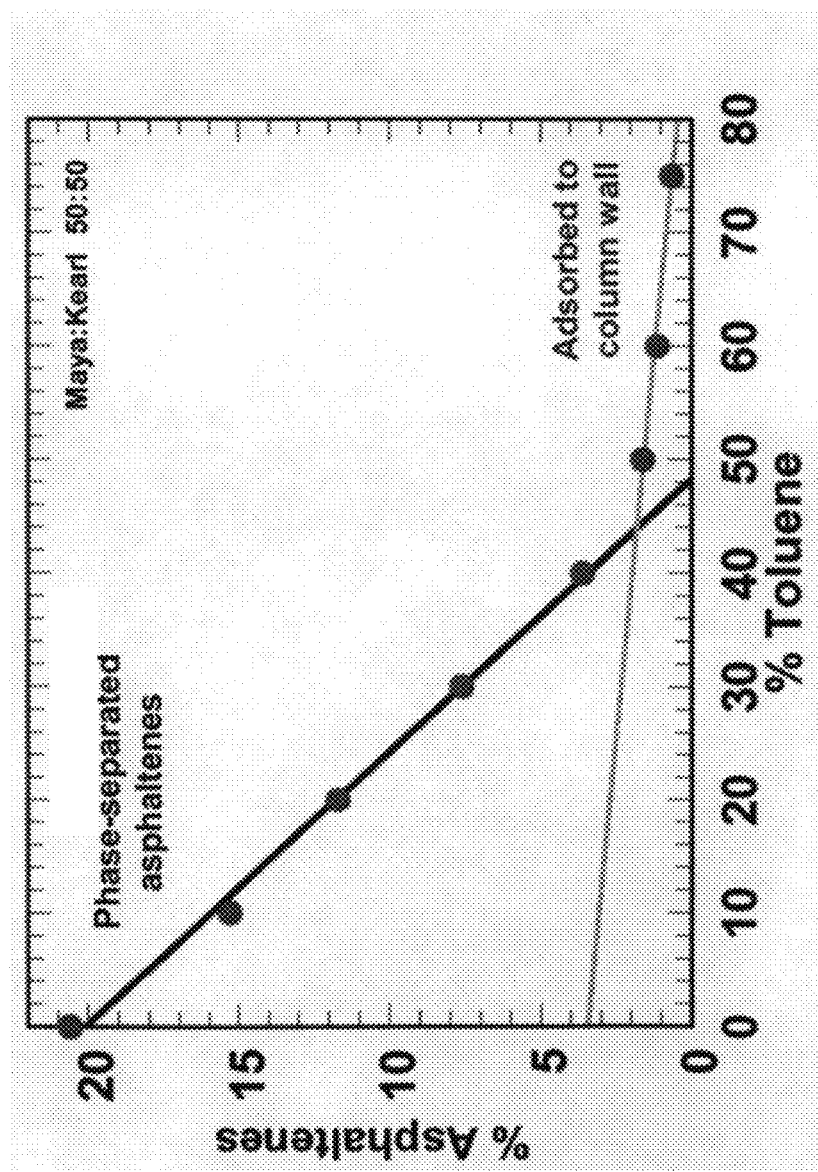

DETERMINATION OF ASPHALTENE SOLUBILITY DISTRIBUTION

CROSS REFERENCE TO RELATED APPLICATIONS

This application claims priority to U.S. Provisional Application Ser. No. 62/875,552 filed Jul. 18, 2019, which is herein incorporated by reference in its entirety.

FIELD

Systems and methods are provided for determining asphaltene content as a function of solubility within a hydrocarbon sample.

BACKGROUND

Various types of heavy petroleum fractions include compounds that can be referred to as asphaltenes. Although various definitions are possible, asphaltenes generally refer to compounds within a petroleum fraction that have multiple aromatic cores, resulting in low solubility/insolubility in various paraffinic compounds.

Characterization of asphaltenes within a petroleum fraction (or other hydrocarbon fraction) can be beneficial for understanding both the solubility characteristics and the processing characteristics of a fraction. Due to the low solubility in paraffinic compounds, petroleum fractions with high asphaltene contents can be incompatible for blending with other fractions that lack sufficient aromatic character. This can lead to precipitation of asphaltenes as solids, which is often undesirable. Asphaltenes can also be difficult compounds to convert by cracking or hydroprocessing, potentially resulting in undesirable coke formation and/or particle formation in some types of processes.

Due to the difficulties presented by some types of asphaltenes, it would be desirable to have improved systems and/or methods for determining the quantity and solubility of asphaltenes within a petroleum fraction. Different types of asphaltenes behave differently in response to fouling, precipitation, and/or other conditions. Thus, having a mechanism for screening the "type of asphaltene" can be valuable.

U.S. Pat. No. 8,241,920 describes processing and analysis techniques for characterizing the asphaltene content of a petroleum fraction. The techniques are performed using a vessel, such as a liquid chromatography column. Instead of using a conventional packing material for performing a separation, the vessel is packed with an inert substrate, such as polytetrafluoroethylene particles. A sample containing asphaltenes and a substance to induce precipitation are introduced into the vessel to cause precipitation of the asphaltenes on the inert substrate. A second solvent (or a plurality of second solvents) is then introduced into the vessel to dissolve the precipitated asphaltenes and carry the asphaltenes out of the vessel. The asphaltenes in the second solvent can then be detected by a suitable method, such as by using an Evaporative Light Scattering Detector. This can allow for automated determination of the amount of asphaltenes in a petroleum sample.

U.S. Pat. No. 5,871,634 describes methods for determining the Solubility Blending Number ($S_{BN}$) and Insolubility Number ($I_N$) for a hydrocarbon sample.

SUMMARY

In various aspects, a method for characterizing a hydrocarbon sample containing asphaltenes is provided. The method can include forming a plurality of solvated samples by combining a hydrocarbon sample comprising asphaltenes with a carrier solvent. The method can further include performing, a plurality of times, an asphaltene characterization. In various aspects, the asphaltene characterization can include introducing a precipitation solvent into a vessel. The vessel can include packing having surfaces comprising a first substantially inert material. The vessel can further include an interior surface comprising a second substantially inert material. The asphaltene characterization can further include passing a solvated sample from the plurality of solvated samples into the vessel to form precipitated asphaltenes. The asphaltene characterization can further include removing the precipitation solvent from the vessel. The asphaltene characterization can further include introducing a dissolution solvent into the vessel to solvate the precipitated asphaltenes. Additionally, the asphaltene characterization can include removing the dissolution solvent from the vessel, and characterizing the solvated asphaltenes in the dissolution solvent.

In some aspects, the precipitation solvent can correspond to a mixture of n-heptane and toluene. This can facilitate calculation of an Insolubilty Number and/or a Solubility Blending Number for the hydrocarbon sample.

BRIEF DESCRIPTION OF THE DRAWINGS

The Figure shows an example of an asphaltene solubility curve determined using a vessel containing polytetrafluoroethylene particles for packing and having stainless steel wall surfaces.

DETAILED DESCRIPTION

All numerical values within the detailed description and the claims herein are modified by "about" or "approximately" the indicated value, and take into account experimental error and variations that would be expected by a person having ordinary skill in the art.

In various aspects, systems and methods are provided for determining an asphaltene solubility distribution for a petroleum sample and/or other hydrocarbon sample. A vessel for performing the method can include both packing material(s) and sidewall(s) that correspond to substantially inert materials. The vessel can initially contain a precipitating solvent suitable for causing precipitation of asphaltenes from a hydrocarbon sample. Examples of a precipitating solvents can correspond to n-heptane, toluene, and mixtures of n-heptane and toluene. The petroleum sample is then introduced into the vessel, along with an optional carrier solvent. The volume of the precipitating solvent can be large relative to the sample, so that the solubility of asphaltenes in the sample becomes dependent on the properties of the precipitating solvent. If asphaltenes are precipitated, the asphaltenes can be washed out of the column using a dissolution solvent, such as chlorobenzene or a mixture of methylene chloride and methanol. The asphaltenes washed out using the dissolution solvent can then be characterized to determine a total asphaltene content. For example, an evaporative light scattering detector can be used to characterize the asphaltenes.

When a combination of two or more solvents are used as a solvent system for the precipitating solvent, such as n-heptane and toluene, this procedure can be repeated with various volume mixtures of n-heptane and toluene. This can provide a solubility distribution for the asphaltenes within the sample. Additionally, a range for the Insolubility Number ($I_N$) can be determined based on the highest volume percentage of toluene that still resulted in asphaltene precipitation and the lowest volume percentage of toluene that did not result in asphaltene precipitation.

It is noted that in the above method, the vessel includes both substantially inert packing material and substantially inert sidewall surfaces. It has been unexpectedly discovered that if conventional sidewall surfaces are used for the vessel, such as stainless steel surfaces, the precipitated asphaltenes can interact strongly with the surfaces. Although packing material typically has substantially more surface area than the interior sidewalls of a vessel containing the packing material, it has further been unexpectedly discovered that the surface area of the sidewalls is large enough to introduce substantial errors into an asphaltene solubility determination. By performing the measurement in a vessel with substantially inert sidewall surfaces, this sidewall adsorption can be reduced or minimized. This allows for an improved measurement of asphaltenes, both in terms of determining a total content as well as determining the solubility distribution.

Methodology

The characterization vessel for performing the asphaltene characterization can be any convenient type of vessel. In some aspects, a high pressure liquid chromatography column can be a suitable type of vessel. One benefit of using a chromatography column is that the asphaltene characterization can be performed using a relatively small amount of sample. For example, in a chromatography column, a solvated sample size of 10 µl to 50 µl, can be sufficient for characterizing the asphaltene content. Additionally, within the solvated sample for characterization, the amount of hydrocarbon sample in the solvated sample can be relatively low, such as 0.5 µl to 10 µl, or 1.0 µl to 10 µl. The low volume required for a characterization can be beneficial when attempting to characterize a crude oil that may not be available in large quantities. For example, when characterizing a bitumen, the hydrocarbon sample for characterization may be derived from a core sample extracted from a oil sands or tar sands extraction site. The amount of bitumen derived from such a core sample can correspond to less than a few milliliters, which can prevent characterization of the sample using many conventional techniques.

The packing material and the sidewalls can have surfaces corresponding to a single substantially inert material or a mixture of inert materials. The packing material and the sidewalls can correspond to the same material or different materials. A substantially inert material refers to a material with a low surface energy for adsorption. Examples of substantially inert materials include, but are not limited to, fluorinated polymers such as polytetraethylfluoride or polyvinylidene fluoride; polyether ether ketone; silicon-based polymers; and polyphenylidene sulfide. The packing material can be composed of the substantially inert material, or the packing material can correspond to another core material that is coated with the substantially inert material. Similarly, the sidewalls of the vessel can be coated with the substantially inert material, or optionally the sidewalls can be composed of the substantially inert material (if that provides sufficient structural integrity). The packing material can correspond to any convenient type of packing material, such as particles, a monolith, a plurality of porous solids, and/or any type of structure typically used for packing material in a chromatography column.

The hydrocarbon sample can correspond to any convenient type of sample that includes asphaltenes. The hydrocarbon sample can correspond to a whole crude or crude fraction. This can include crude oils or crude fractions derived from sources such as tar sands, oil sands, or other sources where bitumen is derived from a non-traditional crude source. The hydrocarbon sample can correspond to a single fraction, or a plurality of fractions can be mixed to form a hydrocarbon sample. In some aspects, the asphaltene content of the hydrocarbon sample can be between 0.1 wt % and 50 wt %, or between 1.0 wt % and 30 wt %. Optionally, a hydrocarbon sample could include up to 100 wt % asphaltenes could be used according to the method described herein.

To prepare for characterization of the asphaltenes in a hydrocarbon sample, the hydrocarbon sample can optionally be mixed with a carrier solvent to form a solvated sample. Forming a solvated sample can facilitate introducing the hydrocarbon sample into the vessel as a liquid. Some asphaltene-containing samples can have a relatively high viscosity even at temperatures as high as 100° C. Mixing the asphaltene-containing sample with a carrier solvent can reduce the viscosity of the combined solvent and sample, so that the combined solvent and sample can be readily passed into the characterization vessel. The carrier solvent can correspond to any convenient solvent that does not induce precipitation of asphaltenes from the sample. Suitable carrier solvents can include, but are not limited to, methylene chloride, chlorobenzene, methanol, and mixtures thereof. For example, a potential carrier solvent can correspond to a 90:10 mixture by volume of methylene chloride and methanol. More generally, any solvent capable of dissolving asphaltenes is potentially suitable as a carrier solvent.

Next, a precipitation solvent can be introduced into the vessel containing the substantially inert packing material and interior sidewall surface(s). In some aspects, a series of precipitation solvents can be used that correspond to mixtures of n-heptane and toluene, n-heptane only, or toluene only. For convenience, references to mixtures of n-heptane and toluene as precipitation solvent are understood to include neat n-heptane and neat toluene, unless otherwise specified. An advantage of using mixtures of n-heptane and toluene as the precipitation solvent is that a Solubility Blending Number ($S_{BN}$) and/or an Insolubility Number ($I_N$) can be determined in the course of performing the methods described herein. However, in other aspects, other precipitation solvents can also be used that provide varying levels of solubility for components (such as asphaltenes) within a hydrocarbon sample. The volume of the precipitation solvent in the vessel can be sufficiently large relative to the volume of the solvated sample so that the precipitation solvent displaces the carrier solvent. In other words, the amount of carrier solvent is small relative to the precipitation solvent, so that the solubility of asphaltenes within the vessel is determined based on the precipitation solvent, with minimal or substantially no influence from the carrier solvent. In some aspects, the amount of precipitating solvent in the vessel can be 1.0 ml or more, or 10 ml or more, such as up to 500 ml or any other convenient amount relative to the size of the vessel. Generally, the amount of precipitation solvent can be large relative to the amount of carrier solvent, so that the volume ratio of precipitation solvent to carrier solvent is 50:1 or more, or 100:1 or more.

The sample and optional carrier solvent can then be introduced into the vessel containing the precipitation solvent. The volume of precipitation solvent can be substantially larger than the volume of the optional carrier solvent, so that any carrier solvent is displaced by the precipitation solvent. Depending on the mixture of n-heptane and toluene (or depending on the nature of another precipitation solvent), the asphaltenes in the sample may be fully compatible with the precipitation solvent, or at least a portion of the asphaltenes may precipitate. It is noted that one definition of asphaltenes is n-heptane insoluble asphaltenes, as defined in ASTM D6560. Thus, when the precipitation solvent corresponds to 100% n-heptane, substantially all of the n-heptane insoluble asphaltenes within a hydrocarbon sample will tend to precipitate.

When asphaltene precipitation occurs, the precipitated asphaltenes can deposit on the surfaces of the packing material and the sidewall surfaces in the vessel. Because the surfaces of the packing material and the sidewall surfaces correspond to a substantially inert material with low surface energy (such as PTFE), there is little or no energy of adsorption between the deposited asphaltenes and the surfaces. This allows the deposited asphaltenes to readily dissolve again when a suitable solvent is introduced into the vessel.

The precipitating solvent and hydrocarbon sample can remain in the column for a period of time to allow precipitation of asphaltenes. A suitable period of time can correspond to 10 seconds or more, or 60 seconds or more, such as up to an hour, a day, or any longer desired period of time. After any precipitation of asphaltenes, the precipitation solvent (including the hydrocarbon sample) can be removed from the vessel. The drain rate of the precipitation solvent from the vessel can be sufficiently slow so that the precipitated asphaltenes remain deposited on the substantially inert surfaces.

A dissolution solvent, which may be the same as the carrier solvent, can then be introduced into the column to dissolve the asphaltenes. The dissolution solvent can be retained in the vessel for a period of time, such as 10 seconds or more, or 60 seconds or more, to allow for dissolution of asphaltenes that were deposited on the substantially inert surfaces. The dissolution solvent can then be removed from the vessel. The dissolution solvent can be selected to correspond to a solvent with a substantially lower boiling point than the asphaltenes. This can allow the dissolution solvent to be separated from the asphaltenes by distillation.

After removal from the vessel, the asphaltenes that were precipitated and then dissolved in the dissolution solvent can be characterized. An Evaporative Light Scattering Detector (ELSD) can be a suitable detector for characterizing the asphaltene content.

The above procedure can be repeated any convenient number of times to allow for characterization of a sample. For example, the above characterization can be performed using neat n-heptane first (to determine the amount of n-heptane asphaltenes), followed by successive mixtures where the amount of toluene is increased by 5 vol % or 10 vol %.

Using mixtures of n-heptane and toluene as the precipitation solvent can allow for several types of characterization of the asphaltenes in a hydrocarbon sample. First, performing a series of tests using different mixtures of n-heptane and toluene can be beneficial for determining the Insolubility Number ($I_N$) of the sample. When a hydrocarbon sample is characterized using a plurality of mixtures of n-heptane and toluene as described herein, the $I_N$ for the sample corresponds to a value between the highest toluene volume percentage that resulted in asphaltene precipitation and the lowest toluene volume percentage that did not result in asphaltene precipitation. More generally, Insolubility Number ($I_N$) and Solubility Blending Number ($S_{BN}$) are defined in U.S. Pat. No. 5,187,634, which is incorporated herein by reference for the limited purpose of describing ($I_N$), ($S_{BN}$), and methods for determining $I_N$ and $S_{BN}$. $I_N$ and $S_{BN}$ provide general measures of the compatibility of a hydrocarbon sample with other types of hydrocarbon samples.

In addition to providing a bounding range for $I_N$, performing a series of tests using various mixtures of n-heptane and toluene can be used to generate an asphaltene solubility curve. The weight of asphaltenes that is precipitated for various amounts of toluene can be determined.

EXAMPLE

A series of 20 µl solvated samples were prepared. The 20 µl solvated samples included 10 vol % of a heavy oil mixture and 90 vol % of carrier solvent. In this example, the carrier solvent was a mixture of methylene chloride and methanol in a 90:10 volume ratio. In other embodimemnts, the carrier solvent can be chlorobenzene. The heavy oil mixture corresponded 50 vol % of a conventional heavy crude oil and 50 vol % of a bitumen formed by paraffinic froth treatment of tar sands. The heavy oil mixture had a density of roughly 1.0 g/ml, so the total amount of heavy oil mixture in the sample, after dilution with the methylene chloride, was roughly $2.0 \times 10^{-3}$ grams.

A liquid chromatography column with stainless steel interior sidewalls was loaded with polytetrafluoroethylene particles as a packing material. A series of tests were then performed using precipitating solvents starting with neat (~100 vol %) n-heptane, with the amount of toluene increased by 10 vol % in successive tests. The precipitating solvent was added to the column. A 20 µl sample was then injected into the column. After waiting for 1 minute to allow for asphaltene formation, the precipitating solvent was drained from the column. Methylene chloride was then added to the column to dissolve any precipitated asphaltenes. After waiting for one minute, the methylene chloride was removed. The methylene chloride, including any dissolved asphaltenes, was then characterized by ELSD to determine the amount of asphaltenes. It is noted that the waiting times in the above procedure is used to provide sufficient time for the precipitating solvent and the dissolution solvent to pass through the column entirely. This reduces or minimizes the possibility of contamination between the solvents. Thus, the waiting time can vary depending on the size of the column.

The weight of asphaltenes detected in the methylene chloride is shown in the Figure. As shown in the Figure, the total n-heptane asphaltenes in the sample was roughly 20.7 wt %. Initially, as the amount of toluene was increased, the amount of asphaltenes precipitated decreased in a linear manner. However, instead of having no precipitated asphaltenes at 50 vol % toluene, instead a new linear behavior was started, where the amount of precipitated asphaltenes decreased more slowly with increasing toluene. The final data point shown in the Figure corresponds to 75 vol % toluene, which resulted in roughly 1.0 wt % of asphaltenes being precipitated and then removed by the methylene chloride.

The data points at 50 vol % toluene or greater corresponded to asphaltene precipitation that was enhanced or facilitated by the stainless steel sidewalls of the column. Another series of samples were tested in a column with the same packing material, but with a polytetrafluoroethylene coating on the interior sidewall of the column. By adding a polytetrafluoroethylene coating on the interior sidewall, at greater than 50 vol % toluene, no asphaltenes were observed in the methylene chloride dissolution solvent.

As illustrated in the Figure, when using a column with substantially inert sidewalls, the $I_N$ determined by the characterization method was less than 50. By contrast, with stainless steel sidewalls, the value of $I_N$ determined by the characterization method would be greater than 75. This is a dramatic difference in the $I_N$ value. Using the higher value of greater than 75 for the IN value would greatly restrict the types of other crude oil fractions the heavy oil could be blended with for things such as pipeline transport or hydroprocessing. By contrast, the $I_N$ determined using the improved column with substantially inert sidewalls was less than 50. An $I_N$ of less than 50 corresponds to a heavy crude oil mixture that can potentially be blended with a wide variety of heavy crude and/or vacuum gas oil fractions without having concerns about solids precipitation. This demonstrates the unexpected and substantial nature of the impact of characterizing asphaltenes using a vessel with substantially inert sidewall surfaces.

Additional Embodiments

Embodiment 1. A method for characterizing a hydrocarbon sample containing asphaltenes, comprising: forming a plurality of solvated samples by combining a hydrocarbon sample comprising asphaltenes with a carrier solvent; and performing, a plurality of times, an asphaltene characterization, the asphaltene characterization comprising: introducing a precipitation solvent into a vessel, the vessel comprising packing having surfaces comprising a first substantially inert material, the vessel further comprising an interior surface comprising a second substantially inert material; passing a solvated sample from the plurality of solvated samples into the vessel to form precipitated asphaltenes; removing the precipitation solvent from the vessel; introducing a to dissolution solvent into the vessel to solvate the precipitated asphaltenes; removing the dissolution solvent from the vessel; and characterizing the solvated asphaltenes in the dissolution solvent.

Embodiment 2. The method of Embodiment 1, wherein a composition of the precipitation solvent is different in each of the plurality of times for performing the asphaltene characterization.

Embodiment 3. The method of any of the above embodiments, wherein the precipitation solvent comprises n-heptane and 0 vol % to 95 vol % toluene.

Embodiment 4. The method of Embodiment 3, wherein the precipitation solvent comprises a different volume percentage of toluene in each of the plurality of times for performing the asphaltene characterization; or wherein during at least one performance of the asphaltene characterization step, the precipitation solvent comprises 5.0 vol % toluene or less; or a combination thereof.

Embodiment 5. The method of Embodiment 3 or 4, wherein the method further comprises determining an Insolubilty Number for the hydrocarbon sample, or wherein the method further comprises determining a Solubility Blending Number for the hydrocarbon sample, or a combination thereof.

Embodiment 6. The method of any of the above embodiments, wherein the hydrocarbon sample comprises one or more petroleum fractions, or wherein the hydrocarbon sample comprises 1.0 wt % to 30 wt % asphaltenes, or a combination thereof.

Embodiment 7. The method of any of the above embodiments, wherein the carrier solvent is the same as the dissolution solvent.

Embodiment 8. The method of any of the above embodiments, wherein the solvated sample comprises a volume of 50 µl or less, or wherein the solvated sample comprises 10 µl of less of the hydrocarbon sample, or a combination thereof.

Embodiment 9. The method of any of the above embodiments, wherein the introduced precipitation solvent comprises a volume of 1.0 ml or more, or wherein a volume ratio of the introduced precipitation solvent to the carrier solvent is 50:1 or more, or a combination thereof.

Embodiment 10. The method of any of the above embodiments, wherein characterizing the solvated asphaltenes in the dissolution solvent comprises characterizing the solvated asphaltenes using an Evaporative Light Scattering Detector.

Embodiment 11. The method of any of the above embodiments, wherein at least one of the carrier solvent and the dissolution solvent comprises methylene chloride, methanol, to chlorobenzene, or a combination thereof.

Embodiment 12. The method of any of the above embodiments, i) wherein the first substantially inert material and the second substantially inert material comprise the same material, or ii) wherein the first substantially inert material comprises polytetrafluoroethylene, or iii) wherein the first substantially inert material comprises a fluorinated polymer, polyether ether ketone, a silicon polymer, or a combination thereof, or iv) a combination of two or more of i), ii), and iii).

Embodiment 13. The method of any of the above embodiments, wherein the vessel comprises a chromatography column.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

The invention claimed is:

1. A method for characterizing a hydrocarbon sample containing asphaltenes, comprising:
   forming a plurality of solvated samples by combining a hydrocarbon sample comprising asphaltenes with a carrier solvent; and
   performing, a plurality of times, an asphaltene characterization, the asphaltene characterization comprising:
      introducing a precipitation solvent into a vessel, the vessel comprising packing having surfaces comprising a first substantially inert material, the vessel further comprising an interior surface comprising a second substantially inert material;
      passing a solvated sample from the plurality of solvated samples into the vessel to form precipitated asphaltenes;
      removing the precipitation solvent from the vessel;
         introducing a dissolution solvent into the vessel to solvate the precipitated asphaltenes;
      removing the dissolution solvent from the vessel; and
      characterizing the solvated asphaltenes in the dissolution solvent.

2. The method of claim 1, wherein the precipitation solvent comprises n-heptane and 0 vol % to 95 vol % toluene.

3. The method of claim 2, wherein the precipitation solvent comprises a different volume percentage of toluene in each of the plurality of times for performing the asphaltene characterization.

4. The method of claim 2, wherein during at least one performance of the asphaltene characterization step, the precipitation solvent comprises 5.0 vol % toluene or less.

5. The method of claim 2, the method further comprising determining an Insolubilty Number for the hydrocarbon sample.

6. The method of claim 2, the method further comprising determining a Solubility Blending Number for the hydrocarbon sample.

7. The method of claim 1, wherein a composition of the precipitation solvent is different in each of the plurality of times for performing the asphaltene characterization.

8. The method of claim 1, wherein the hydrocarbon sample comprises one or more petroleum fractions.

9. The method of claim 1, wherein the hydrocarbon sample comprises 1.0 wt % to 30 wt % asphaltenes.

10. The method of claim 1, wherein the carrier solvent is the same as the dissolution solvent.

11. The method of claim 1, wherein the solvated sample comprises a volume of 50 µl or less.

12. The method of claim 1, wherein the solvated sample comprises 10 µl of less of the hydrocarbon sample.

13. The method of claim 1, wherein the introduced precipitation solvent comprises a volume of 1.0 ml or more.

14. The method of claim 1, wherein a volume ratio of the introduced precipitation solvent to the carrier solvent is 50:1 or more.

15. The method of claim 1, wherein characterizing the solvated asphaltenes in the dissolution solvent comprises characterizing the solvated asphaltenes using an Evaporative Light Scattering Detector.

16. The method of claim 1, wherein at least one of the carrier solvent and the dissolution solvent comprises methylene chloride, methanol, chlorobenzene, or a combination thereof.

17. The method of claim 1, wherein the first substantially inert material and the second substantially inert material comprise the same material.

18. The method of claim 1, wherein the first substantially inert material comprises polytetrafluoroethylene.

19. The method of claim 1, wherein the first substantially inert material comprises a fluorinated polymer, polyether ether ketone, a silicon polymer, or a combination thereof.

20. The method of claim 1, wherein the vessel comprises a chromatography column.

* * * * *